(12) United States Patent
Hansen

(10) Patent No.: US 8,087,524 B2
(45) Date of Patent: Jan. 3, 2012

(54) CONTAINER, IN PARTICULAR AN AMPOULE

(76) Inventor: Bernd Hansen, Sulzbach-Laufen (DE)

( * ) Notice: Subject to any disclaimer, the term of this patent is extended or adjusted under 35 U.S.C. 154(b) by 1113 days.

(21) Appl. No.: 11/664,616

(22) PCT Filed: Oct. 14, 2005

(86) PCT No.: PCT/EP2005/011057
§ 371 (c)(1),
(2), (4) Date: Apr. 4, 2007

(87) PCT Pub. No.: WO2006/048105
PCT Pub. Date: May 11, 2006

(65) Prior Publication Data
US 2007/0262045 A1 Nov. 15, 2007

(30) Foreign Application Priority Data

Nov. 8, 2004 (DE) .................. 10 2004 054 151
Nov. 8, 2004 (DE) .................. 20 2004 017 346 U

(51) Int. Cl.
*B65D 41/32* (2006.01)
*A61J 1/06* (2006.01)
(52) U.S. Cl. .............. 215/253; 222/541.6; 206/222; 215/10; 215/48
(58) Field of Classification Search ............... 215/253, 215/10, 48; 222/541.6; 220/23.2, 23.4, 23.83; 446/117, 121; 206/219, 222
See application file for complete search history.

(56) References Cited

U.S. PATENT DOCUMENTS

| 4,871,091 | A  | * | 10/1989 | Preziosi ............... 222/92 |
| 5,401,200 | A  | * | 3/1995 | Ellis ................. 446/71 |
| 6,276,549 | B1 | * | 8/2001 | Fasci et al. .......... 220/23.4 |
| 7,644,828 | B1 | * | 1/2010 | Klein ................. 215/10 |
| 2002/0066748 | A1 | * | 6/2002 | Weiler et al. ......... 222/129 |
| 2003/0140921 | A1 |  | 7/2003 | Smith et al. |
| 2004/0139968 | A1 |  | 7/2004 | Loeffler et al. |

FOREIGN PATENT DOCUMENTS

| DE | 35 25 098 | 1/1987 |
| DE | 38 33 036 | 4/1990 |
| EP | 0 930 238 | 7/1999 |
| GB | 2 362 147 | 11/2001 |

* cited by examiner

*Primary Examiner* — Anthony Stashick
*Assistant Examiner* — James N Smalley
(74) *Attorney, Agent, or Firm* — Roylance, Abrams, Berdo & Goodman, L.L.P.

(57) ABSTRACT

A container, in particular an ampoule, has at least one layer of plastic material and a discharge chamber (10). A discharge medium can be stored and discharged via at least one container opening (12) which can be closed by a closeable closing part (14). The discharge chamber (10) includes at least one additional container opening (16) which can be closed by an additional closeable closing part (18). For an individual container, at least two different types of container openings (12, 16) are provided which are economical to produce and can lead to a plurality of connection solutions.

19 Claims, 1 Drawing Sheet

CONTAINER, IN PARTICULAR AN AMPOULE

FIELD OF THE INVENTION

The present invention relates to a container, in particular an ampoule, having at least one layer of plastic material and a delivery chamber in which at least one delivery medium can be stored. The delivery medium can be delivered via at least one container opening which can be closed by a detachable closure part.

BACKGROUND OF THE INVENTION

DE 38 33 036 C2 discloses a double chamber container, especially a double chamber ampoule, with two chambers formed by two receptacles located in parallel next to one another. The chambers have removable closures molded to a single twist closure. In the known solution the two receptacles are detachably connected to one another. The neck part of one receptacle forming the fill and/or removal opening is provided with a conical outer jacket surface tapering toward the free end of this neck part. The neck part of the other receptacle forms the fill and/or removal opening and is provided with an inner cone made to correspond to the outer cone of the other receptacle and tapering against the interior of the container.

With the known double chamber solution, the contents of the two containers can be brought together and mixed without an additional receptacle being necessary for this purpose. The tight plug closure by the cones allows the two receptacles to be shaken in the known solution. Because the two closures are molded onto a single twist closure, they can be removed from the neck part bearing them essentially at the same time using this twist closure. A mixing process can then be initiated. If in the known solution at least one of the two receptacles can be deformed, before producing the plug connection it can be somewhat compressed, resulting in a slight underpressure by which the liquid (delivery medium) can be sucked out of the other container. The neck part of one container forming an inner cone for ampoules is advantageously made according to the standards for medical devices, so that the cone of a syringe can be inserted into the neck part. It is possible not to fill one receptacle. In the joined state a relatively large amount of space is then available. This can be advantageous for example when the contents of the filled receptacle must be moved back and forth or vigorously shaken before use, for example, to facilitate its application.

The disadvantage of the known solution is that each container always has only one special type of container opening so that only pairs can ever be connected to one another with their corresponding associated delivery openings. Since these containers are generally combined in a configuration of several next to one another in blocks of ampoules, problems can arise when the pertinent pairs, especially after their separation from the ampoule block, must be properly collected and matched. If the containers are used individually, it cannot be precluded that for the intended connection possibility in the form of the delivery openings on the respective delivery chambers no direct and proper filling and/or removal connection is on site. Furthermore, in the known solution production costs are increased since tools for two different types of containers must be made available.

SUMMARY OF THE INVENTION

An object of the invention is to provide an improved container avoiding the above-described disadvantages that in particular can be produced favorably in terms of production technology and has higher variance with respect to its connection systematics.

This object is basically achieved by a container were the delivery chamber has at least one further container opening which can be closed respectively by another detachable closure part. The individual container has at least two different types of container openings when made appropriately. The container can then be connected to the respectively other type of container opening, when an adjacent ampoule or an adjacent container which is made exactly the same as the indicated container. While retaining the advantages of the double chamber solution in the prior art, only one type of container is required such that the tools and accordingly the production costs can be reduced.

The container according to the invention with its different types of container openings can be coupled to existing removal systems on site by properly coupling an existing fill and/or removal connection to one of the existing types of container openings which meet medical standards in this respect.

Preferably, the respective container opening forms a fill and/or removal point for the respective delivery medium and is located on the free end of the neck part undergoing transition into the delivery chamber. The various types of container openings have neck configurations which are different from one another for connecting different fill and/or removal connections. If preferably one type of container opening has a neck part tapering conically towards its free end with its outer jacket surface or is cylindrical, and the other type of container opening has another neck part which widens conically towards its free end with its inner jacket surface or is cylindrical, both standardized male and also female connection points, which in technical terms are also called Luer locks, are designed for the container.

In an especially preferred embodiment of the container according to the invention, the delivery chamber and/or the respective neck part have at least one catch for engaging at least one corresponding catch means of the respective fill and/or removal connection. In addition to a reliable fixing possibility of the respective connection to the container, plausibility checking is redundantly possible for matching the applied connection to the associatable delivery opening, in any event when the corresponding catch appropriately interact with one another.

Other objects, advantages and salient features of the present invention will become Apparent from the following detailed description, which, taken in conjunction with the annexed drawings, discloses a preferred embodiment of the present invention.

BRIEF DESCRIPTION OF THE DRAWINGS

Referring to the drawings which form a part of this disclosure and which are schematic And not to scale.

DETAILED DESCRIPTION OF THE INVENTION

Figure 1:
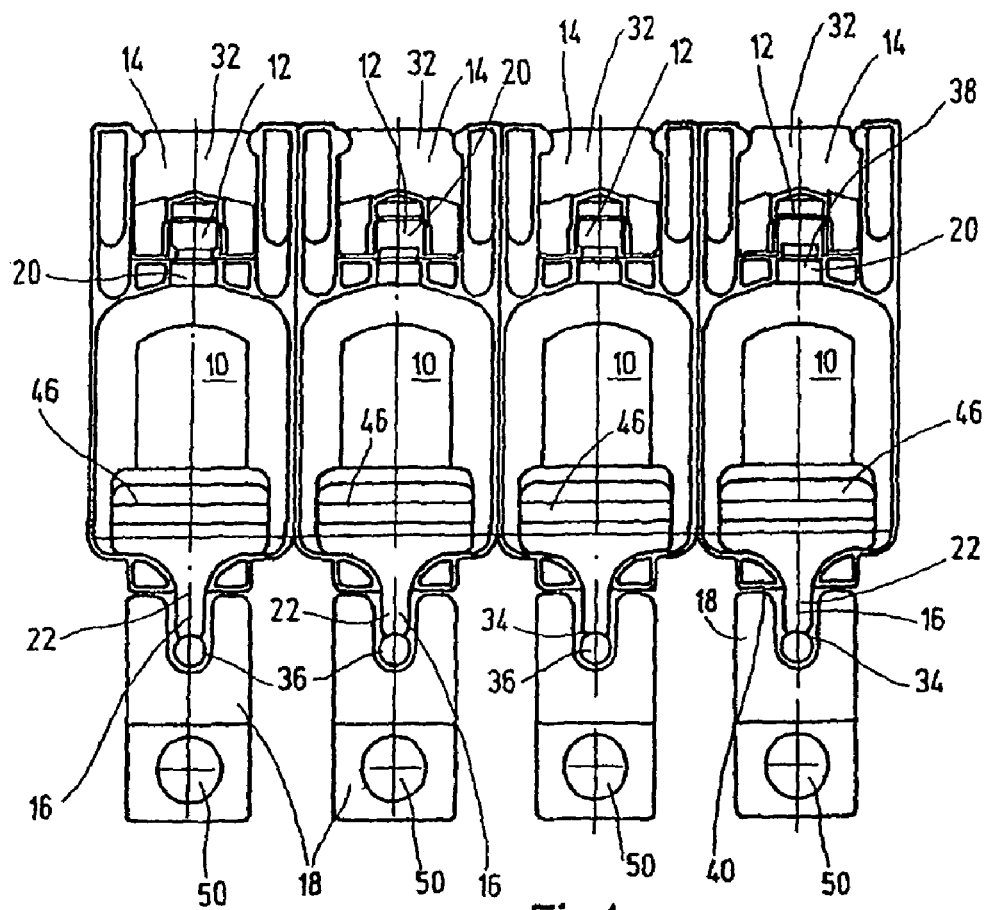
FIG. 1 is a front elevational view of an ampoule block with a total of four individual containers according to one exemplary embodiment of the present invention.

The ampoule block shown in FIG. 1 is shown only incompletely and depicts a total of four containers. The row of containers can be continued accordingly to both sides. The individual containers are shaped in the blow molding process or by means of a vacuum from plastic materials accordingly suited for this purpose. The containers can be produces using the bottelpack® process in which in a working station the containers are blow-molded, filled under sterile conditions and sealed. During the simultaneous formation of both of two adjacent containers, between the body of the two containers a parting zone holding them together is produced and keeps the two adjacent containers connected to one another. The two adjacent containers can be separated by the container being moved relative to one another around the parting zone.

Each container has a delivery chamber 10 in which a delivery medium can be stored. The individual containers of an ampoule block can have the same delivery medium or different delivery mediums that can be mixed with one another. The delivery chamber 10 can be empty or can store a gaseous medium therein which then accordingly interacts optionally with the delivery media of the adjacent containers. The delivery medium can be delivered via a container opening 12 which can be closed by a detachable closure part 14. Furthermore, the respective delivery chamber 10 has at least one other or a second container opening 16 which can be sealed by another or a second detachable closure part 18.

The respective container opening 12, 16 forms a filling and/or removal point for the respective delivery medium. The point is located on the free end of the neck part 20 or 22 undergoing transition into the delivery chamber 10. The different types of container openings 12, 16 having neck configurations 20, 22 differing from one another for connecting different fill and/or removal connections, especially in the form of the corresponding neck parts 22 and 20 of another container.

One type of container opening 16 has a neck part 22 tapering conically towards its free end with its outer jacket surface, while the other type of container opening 12 has a neck part 20 made essentially cylindrical. Neck part 20 can also widen conically toward its free end with its inner jacket surface. In particular, in one cylindrical configuration a corresponding calibration is provided to ensure a good fitting seat with the cone to be inserted, for example, in the form of the neck part 22.

Figure 3:
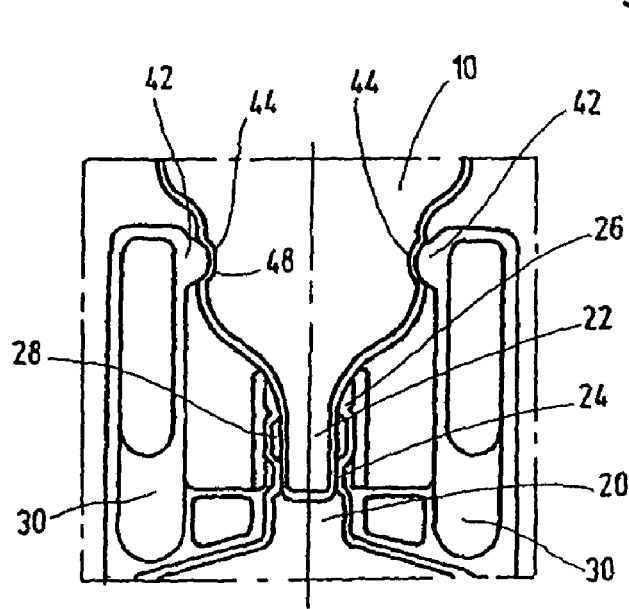
FIG. 3 is an enlarged partial front elevational view of the container connection in which the top part of a container is connected via a Luer lock connection to the bottom part of another container of FIG. 1.
Figure 2:
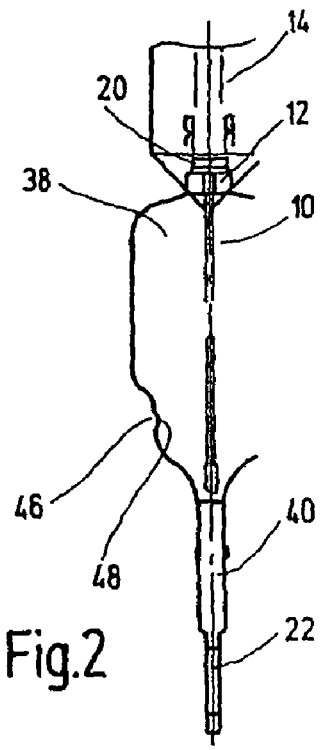
FIG. 2 is a partial side elevational view of an individual container of FIG. 1.

This connection situation is shown in FIG. 3. Neck part 20 of the subjacent container has a first cylindrical fitting surface 24. Neck part 22 has another second, overlying fitting surface 26. Between the two fitting surfaces 24 and 26 within the neck part 20 there is a cavity 28 which together with the conical outer jacket surface of the penetrating neck part 22 ensures that sterile-sealing contact via the fitting surfaces 24, 26 occurs. For precision-fitting contact, the stiffening crosspieces 30 extend on either side and form a corresponding counterstay to the spreading motion relative to the neck part 20. These stiffening crosspieces 30 are initially a component of the closure part 14. After removing the middle part 32 of the closure part 14, the container opening 12 is cleared for engagement of the male engagement part 22. The closure parts 14, 18 are thus made at least partially as a twist closure which are conventional in this domain. After removal of the twist closures along a given weakened parting site, a removal opening can be cleared for the pertinent ampoule products. In the other lower closure part 18, this parting site 34 is detachably closed by a closure ball 36 as part of the other closing part 18. According to the illustrated embodiment, therefore the respectively different types of container openings 12, 16 are located on end sides 38, 40 facing away from one another (top and bottom side).

According to the present invention, in the radial transverse widening to the neck part 20 on the top side of the container and in the above extension of the respective stiffening crosspiece 30 a first catch 42 is provided in the form of a catch projection which can be detachably locked into a corresponding recess as another or second catch 44 on the bottom of the delivery chamber of the other container. For this purpose, the recess 44 is made as a concave depression into which the catch projection of the catch means 42 can convexly lock, projecting in an elastically flexible form. For this engagement, as shown in FIG. 1, the lower end region of the delivery chamber 10 is provided superficially with fluting 46. An interposed engagement groove 48 forms the recess 44. In an embodiment (not shown) these catches can be omitted with the connection produced only via the conventional Luer lock systematics.

Instead of the illustrated interfitting of the two containers as shown in FIG. 3, it is also possible to couple the respective container to an external connection to effect a removal process. Based on the two different removal systems on the top and on the bottom side of each container the removal possibility is enhanced relative to the medically standardized connection sites provided for this purpose. Furthermore, the container in at least one direction can have fixing openings 50, for example, for attaching product information, patient data or the like. In this way, for the purposes of a drip solution via the fixing opening 50 the respective container could be suspended on a structure intended for this purpose (not shown). It is possible to couple more than two containers to one another in a row so that within a larger framework the most varied mixtures can be prepared.

To produce the container a so-called bottelpack® coextrusion process can also be used in which the plastic material is extruded in a tube shape and is placed against the inside walls of a shaping tool for shaping the respective container by differential pressure (blow molding). The respective container is filled via at least one of its container openings 12, 16 using a filling mechanism with the respective delivery medium. The container opening 12, 16 is closed under sterile conditions by sealing. For extrusion various plastic materials can then be used in the coextrusion process in which the respective container is built up at least partially from several layers of plastic materials, preferably at least one of the layers being used as a blocking layer. The individual layers can be formed from different plastic materials, especially polyolefin, polyamide, polypropylene, low density polyethylene, copolymers and ethylene-vinyl alcohol copolymers.

While one embodiment has been chosen to illustrate the invention, it will be understood by those skilled in the art that various changes and modifications can be made therein without departing from the scope of the invention as defined in the appended claims.

The invention claimed is:
1. A container, comprising:
a container body of at least one layer of plastic material;
a delivery chamber within said container body for storing a delivery medium;
first and second neck parts extending from said chamber and having different configurations for different fill/removal connections, said first neck part having an outer surface being one of tapering conically toward said free end thereof and extending cylindrically, said second neck part having an inner surface being one of widening conically toward said free end thereof and extending cylindrically;

a first container opening on a free end of said first neck part and providing access to said chamber to fill and remove the delivery medium into and out of said chamber;
a first detachable closure releasably closing said first container opening;
a second container opening on a free end of said second neck part and providing access to said chamber to fill and remove the delivery medium into and out of said chamber; and
a second detachable closure having stiffening crosspieces initially formed as parts thereof, having a removable middle part releasably coupled between said crosspieces and releasably closing said second container opening, said stiffening crosspieces having catch projections thereon, removal of said middle part clearing said second opening and exposing said catch projections to engage a mating catch on an ampule to mate therewith.

2. A container according to claim 1 wherein
said first and second container openings face away from one another coaxially to a longitudinal axis of said chamber on opposite ends of said chamber.

3. A container according to claim 1 wherein
said closure parts comprise twist closures.

4. A container according to claim 1 wherein
said first neck parts has a catch releasably engagable with said catch projections.

5. A container according to claim 1 wherein
a laterally closed fixing opening for attaching information data extends from one of said container openings.

6. A container according to claim 1 wherein
said container body has several layers of plastic produced by coextrusion.

7. A container, comprising:
a container body of at least one layer of plastic material;
a delivery chamber within said container body for storing a delivery medium;
first and second neck parts extending from said chamber and having different configurations for different fill/removal connections;
a first container opening on a free end of said first neck part and providing access to said chamber to fill and remove the delivery medium into and out of said chamber;
a first detachable closure releasably closing said first container opening;
a second container opening on a free end of said second neck part and providing access to said chamber to fill and remove the delivery medium into and out of said chamber;
a second detachable closure having stiffening crosspieces initially formed as parts thereof, having a removable middle part releasably coupled between said crosspieces and releasably closing said second container opening, said stiffening crosspieces having catch projections thereon, removal of said middle part clearing said second opening and exposing said catch projections to engage a mating catch on an ampule to mate therewith; and
a mating recess on said first neck part.

8. A container according to claim 7 wherein
said container body has several layers of plastic produced by coextrusion.

9. A container according to claim 7 wherein
a laterally closed fixing opening for attaching information date extends from one of said container openings.

10. A container according to claim 7 wherein
said closure parts comprise twist closures.

11. A container according to claim 7 wherein
said first and second container openings face away from one another coaxially to a longitudinal axis of said chamber on opposite ends of said chamber.

12. A container according to claim 1 wherein
said stiffening crosspieces extend parallel to a longitudinal axis of said container body, with said projections extending radially inwardly toward said longitudinal axis.

13. A container according to claim 7 wherein
said stiffening crosspieces extend parallel to a longitudinal axis of said container body, with said projections extending radially inwardly toward said longitudinal axis.

14. A container, comprising:
a container body of at least one layer of plastic material;
a delivery chamber within said container body for storing a delivery medium;
first and second neck parts extending from and being a single piece of plastic material with said container body, and having different mating configurations for different fill/removal connections;
a first container opening on a free end of said first neck part and providing access to said chamber to fill and remove the delivery medium into and out of said chamber;
a first detachable closure releasably closing said first container opening and being a single piece of plastic material with said container body and said neck parts;
a second container opening on a free end of said second neck part and providing access to said chamber to fill and remove the delivery medium into and out of said chamber; and
a second detachable closure releasably closing said second container opening and being a single piece of plastic material with said container body, said neck parts and said first detachable closure, said container openings being unobstructed except for said detachable closures, said second detachable closure having stiffening crosspieces initially formed as parts thereof and a removable middle part releasably coupled between said crosspieces, said stiffening crosspieces having catch projections thereon, removal of said middle part clearing said second opening and exposing said catch projections to engage a mating catch on an ampule to mate therewith.

15. A container according to claim 14 wherein
said container body has several layers of plastic produced by coextrusion.

16. A container according to claim 14 wherein
a laterally closed fixing opening for attaching information date extends from one of said container openings.

17. A container according to claim 14 wherein
said closure parts comprise twist closures.

18. A container according to claim 14 wherein
said first and second container openings face away from one another coaxially to a longitudinal axis of said chamber on opposite ends of said chamber.

19. A container according to claim 14 wherein
said stiffening crosspieces extend parallel to a longitudinal axis of said container body, with said projections extending radially inwardly toward said longitudinal axis.

* * * * *